United States Patent [19]

Mészáros et al.

[11] 4,089,858

[45] May 16, 1978

[54] HETEROCYCLIC-AMINO-ACRYLIC ACID DERIVATIVES

[75] Inventors: Zoltán Mészáros; József Knoll; István Hermecz; Piroska Simon; Peter Szentmiklosy; Lelle Vasvári; Ágnes Horvath; Gabor Horvath, all of Budapest; Peter Dvortsák, Ocsa, all of Hungary

[73] Assignee: Chinoin Gyógyszer és Vegyészeti Termékek Gyára Rt., Budapest, Hungary

[21] Appl. No.: 614,208

[22] Filed: Sep. 17, 1975

Related U.S. Application Data

[63] Continuation of Ser. No. 330,125, Feb. 6, 1973, abandoned.

[51] Int. Cl.² .......................................... C07D 213/02
[52] U.S. Cl. ............................ 260/295 R; 260/287 F; 260/287 AR; 260/295 AM; 260/295.5 A; 260/295.5 R; 544/356; 544/336; 544/405; 544/408; 544/409; 544/406; 544/407; 544/292; 544/293; 544/332; 544/329; 544/322
[58] Field of Search ............ 260/240 G, 295 R, 268 R, 260/256.4 N, 295 AM, 250 B, 256.4 Q, 287 AR, 287 F, 295.5 A

[56] References Cited

PUBLICATIONS

Klingsberg, Pyridine and Its Derivatives, Part Three, pp. 20 and 45, and front page, Interscience Publishers (1962).
Lappin, J. Am. Chem. Soc. vol. 70, pp. 3348 to 3349 (1948).
Antaki, J. Am. Chem. Soc. vol. 80, pp. 3066 to 3069 (1958).
Hauser et al, J. Org. Chem col. 14, pp. 453 to 459 (1949).
Rubtsov, J. Gen. Chem. (USSR) vol. 9, pp. 1517 to 1524 (1939).
Chemical Abstracts vol. 34, col. 2845 (1940) (abst. of Rubtsov).

*Primary Examiner*—Alan L. Rotman
*Attorney, Agent, or Firm*—Karl F. Ross

[57] ABSTRACT

The present invention is concerned with the preparation of chemical intermediates, namely, beta-aminoacrylic acid ester derivatives of nitrogen heterocycles, i.e. pyridine, quinoline, quinoxaline, pyrazine, pyrimidine and the like. Said intermediates are cyclized to form pyrido-pyrimidine type final products possessing analgesic activity.

2 Claims, No Drawings

HETEROCYCLIC-AMINO-ACRYLIC ACID DERIVATIVES

This is a continuation of application Ser. No. 330,125, filed Feb. 6, 1973 (now abandoned).

It is known that on reacting aniline with 2-formyl-phenyl-ethyl-acetate, α-phenyl-β-phenylamino-ethylacrylate is formed. Similar reaction takes place when using p-toluidine and p-xylidine [Börner: Dissertation. (Wurzburg. 1899) 37–41; Beilstein 10, 688].

According to a feature of the present invention, there are provided new 3-amino-acrylic acid derivatives of the Formula I

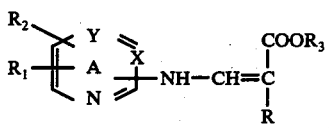

and salts thereof,
(wherein
R stands for an optionally substituted alkyl, aryl or aralkyl group or a group of the formula $-(CH_2)_n-COOR_4$ in which $n$ is 1, 2 or 3 and $R_4$ is hydrogen, alkyl or aralkyl;
$R_1$ and $R_2$ are hydrogen or together form a group of the formula $-CH=CH-CH=CH-$ attached to positions 2,3—or 3,4;
Ring-A may bear optionally one or more substituents;
X and Y stand for $-CH=$ or $-N=$ whereby at least one of the symbols X and Y is $-CH=$;
$R^3$ is hydrogen, alkyl or aralkyl).

The present invention encompasses all the tautomeric forms of the compounds of the formula I and the preparation thereof. Some of the possible isomers are illustrated in the Formulae:

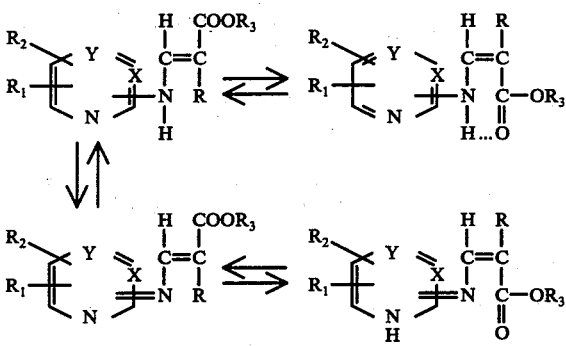

The ring-A may optionally bear one or more substituents selected preferably from the following group: alkyl (e.g. methyl, ethyl, propyl), nitro, halogen (e.g. chlorine or bromine), hydroxy, alkoxy (e.g. methoxy or ethoxy), carboxy, alkoxycarbonyl (e.g. ethoxycarbonyl), carboxamido, amino, alkylamino, (e.g. methylamino), dialkylamino (e.g. dimethylamino), acylamino (e.g. acetylamino).

The group R stands preferably for an alkyl group (e.g. methyl or ethyl), a phenyl group, an aralkyl group (e.g. benzyl) or a substituted alkyl group (e.g. $-CH_2-COOC_2H_5$, $-(CH_2)_2-COOC_2H_5$ or $-(CH_2)_3-COOC_2H_5$).

$R_3$ is preferably hydrogen or an alkyl group (e.g. methyl).

Particularly preferred representatives of the compounds of the formula I are the derivatives enumerated in the examples. The first compound of Example 1 is especially advantageous.

According to the present invention there is also provided a process for the preparation of compounds of the formula I, tautomeric forms and salts thereof which comprises reacting a compound of the formula II

(wherein $R_1$, $R_2$, X, Y and A have the same meaning as stated above) with a 2-formyl-acetic acid derivative of the formula III

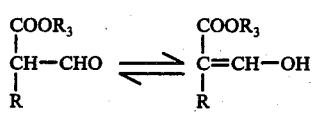

(wherein R and $R_3$ have the same meanings as stated above),
if desired esterifying an acid of the formula I in which $R_3$ is hydrogen, if desired converting an ester of the formula I, in which $R_3$ is alkyl or aralkyl, into the corresponding acid and if desired converting a compound of the formula I thus obtained into its salt.

The reaction between a compound of the formula II and a compound of the formula III may be carried out by stirring the reaction mixture at room temperature or at elevated temperature (e.g. at 100° C).

The condensation reaction may be carried out in an inert solvent. For this purpose e.g. hydrocarbons (such as benzene, toluene etc.), partially or completely halogeneted hydrocarbon derivatives (e.g. dichloromethane, carbon tetrachloride, dichloroethane etc.), alcohols (such as ethanol, n-butanol etc.) ethers (e.g. dioxane etc.), tertiary bases (e.g. pyridines etc.), esters (e.g. ethyl acetate) or mixtures thereof may be used.

The reaction products may be isolated by methods known per se.

Compounds of the formula I, in which $R_3$ is hydrogen, may be esterified by known methods. One may proceed by treating the free carboxylic acid with diazomethane or reacting the acid with a thionyl halide /e.g. thionyl chloride) and treating the acid halide thus obtained with an alcohol to yield the desired esters.

Esters of the formula I, in which $R_3$ is alkyl or aralkyl, may be hydrolysed by known methods into the corresponding carboxylic acid. One may proceed by e.g. by hydrolysing the ester with an aqueous alkali metal hydroxide solution (e.g. with sodium hydroxide) and acidifying with a mineral acid (e.g. hydrochloric acid).

The compounds of the formula I may be converted, if desired, into the salts thereof. Inorganic acids (such as hydrochloric acid, sulfuric acid, phosphoric acid, perchloric acid etc.) and organic acids (e.g. citric acid, amygdalic acid, malic acid etc.) may be used for salt-formation.

The compounds of the formula I are useful intermediates in the preparation of compounds of the formula I. Thus compounds of the formula I, wherein X and Y are $-CH=$, may be subjected to cyclization to yield homopyrimidazole derivatives which are active on the central nervous system and exert an analgetic effect.

Further details of the present invention are to be found in the Examples without limiting the scope of the invention to the Examples.

The starting materials of the formulae II and III are known compounds which may be prepared by known methods.

EXAMPLE 1

9.4 g. (0.1 mole) of 2-amino-pyridine, 20.2 g. (0.1 mole) of 2-formylsuccinic acid diethylester and 100 ml. of dichloromethane are refluxed for 3 hours, while the water formed in the condensation reaction is continuously removed. After removal of the solvent the crude α-(ethoxycarbonyl-methyl)-β-(2-pyridyl-amino)-acrylic acid ethyl ester is purified by crystallization from 50% alcohol. Yield 65–70%. M.p.: 117°–118° C.

Analysis: C% 60.77 (calc. 60.70); H% 6.68 (calc. 6.48); N% 10.28 (calc. 10.05).

The above reaction is carried out with the difference that other amine components are used. The following acrylic acid derivatives are obtained:

from 6-ethyl-2-amino-pyridine: α-(ethoxycarbonyl methyl)-β-(6-ethyl-2-pyridyl-amino-acrylic acid ethyl ester. M.p.: 99° C; Yield: 60–65%;

from 4,6-dimethyl-2-amino-pyridine α-(ethoxycarbonyl-methyl)-β-(4,6-dimethyl-2-pyridyl-amino)-acrylic acid ethyl ester. M.p.: 136°–137° C; Yield: 66–70%;

from 3-hydroxy-2-amino-pyridine α-(ethoxycarbonyl-methyl)-β-(3-hydroxy-2-pyridyl-amino)-acrilic acid ethyl ester. M.p.: 142°–143° C; Yield: 55%;

from 3-amino-pyridine α-(ethoxycarbonyl-methyl)-β-(3-pyridyl-amino)-acrylic acid ethyl ester. M.p.: 90°–92° C; Yield: 30%;

from 5-chloro-2-amino-pyridine α-(ethoxycarbonyl-methyl)-β-(5-chloro-2-pyridyl-amino)-acrylic acid ethyl ester. M.p.: 138° C; Yield 70–75%;

from 6-hydroxy-2-amino-pyridine α-(ethoxycarbonyl-methyl)-β-(6-hydroxy-2-pyridyl-amino)-acrylic acid ethyl ester,. M.p.: 125° C; Yield: 10–15% are obtained.

EXAMPLE 2

13.9 g. (0.1 mole) of 5-nitro-2-amino-pyridine and 20.2 g. (0.1 mole) of 2-formyl-succinic acid diethylester are stirred in 150 ml. of pyridine at 40°–50° C for 3 hours. After removing the solvent, the crude α-(ethoxycarbonyl-methyl)-β-(5-nitro-2-pyridyl-amino)-acrylic acid ethyl ester is crystallized from 50% ethanol. Yield: 25 – 30%; m.p.: 167°–168° C.

Analysis: C% 52.25 (calc. 52.10); H% 5.07 (calc. 5.27); N% 13.17 (calc. 13.00).

EXAMPLE 3

10.8 g. (0.1 mole) of 3-methyl-2-amino-pyridine are admixed with 20.2 g. (0.1 mole) of 2-formyl-succinic acid diethyl ester. The reaction mixture warms up to 40°–50° C. The mixture is stirred for an hour, whereupon it is allowed to stand at room temperature overnight. The α-(ethoxycarbonyl-methyl)-β-(3-methyl-2-pyridyl-amino)-acrylic acid ethyl ester thus obtained is recrystallized from 50% aqueous ethanol. Yield: 65–70%, m.p.: 62° C.

Analysis: C% 62.02 (calc. 61.80); H% 6.97 (calc. 6.85); N% 9.71 (calc. 9.60).

EXAMPLE 4

10.8 g. (0.1 mole) of 6-methyl-2-amino-pyridine and 21.6 g. (0.1 mole) of 2-formyl-glutaric acid diethyl ester are heated to boiling in 100 ml. of carbon tetrachloride for 3 hours. After removing the solvent, the crude β-(2-ethoxycarbonyl-ethyl)-β-(6-methyl-2-pyridyl-amino)-acrylic acid ethyl ester is crystallized from petrolether. Yield: 55%; m.p.: 63°–65° C.

Analysis: C% 62.75 (calc. 62.67); H% 7.30 (calc. 7.23); N% 9.24 (calc. 9.14).

The above condensation is carried out with the difference that further amine components are used. The following acrylic acid derivatives are obtained:

from 2-amino-pyridine α-(2-ethoxycarbonyl-ethyl)-β-(2-pyridyl-amino)-acrylic acid ethyl ester; m.p.: 112°–114° C; Yield: 75%;

from 5-methyl-2-amino-pyridine α-(2-ethoxycarbonyl-ethyl)-β-(5-methyl-2-pyridyl-amino)-acrylic acid ethyl ester; m.p.: 89°–90° C; yield: 40–45%;

from 4-methyl-2-amino-pyridine α-(2-ethoxycarbonyl-ethyl)-β-(4-methyl-2-pyridyl-amino)-acrylic acid ethyl ester, m.p.: 135° C; yield: 30–35%.

The above reaction is carried out by using the corresponding amines and formyl acetic acid derivative. The following acrylic acid derivatives are obtained:

from 6-methyl-2-amino-pyridine and 2-formyl-propionic acid ethyl ester α-methyl-β-(6-methyl-2-pyridyl-amino)-acrylic acid ethyl ester, m.p.: 120°–121° C; yield: 80%;

from 5-methyl-2-amino-pyridine and 2-formyl-propionic acid ethyl ester: α-methyl-β-(5-methyl-2-pyridyl-amino)-acrylic acid ethyl ester, m.p.: 135°–136° C; yield: 40%;

from 4,6-dimethyl-2-amino-pyrimidine and 2-formyl-succinic acid diethyl ester: α-(ethoxycarbonyl-methyl)-β-(4,6-dimethyl-2-pyridyl-amino)-acrylic acid ethyl ester; m.p.: 130°–131° C; yield: 35–40%;

from 3-amino-pyridine and 2-formyl-propionic acid ethyl ester α-methyl-β-(3-pyridyl-amino)-acrylic acid ethyl ester, m.p.: 148° C; yield 30–35%;

from 6-ethyl-2-amino-pyridine and 2-formyl-phenylacetic acid ethyl ester: α-phenyl-β-(6-ethyl-2-pyridyl-amino)-acrylic acid ethyl ester, m.p.: 67° C; yield: 40–45%;

from 3-methyl-2-amino-pyridine and 2-formyl-phenyl-acetic acid ethyl ester α-phenyl-β-(3-methyl-2-pyridyl-amino)-acrylic acid ethyl ester, m.p.: 88°–90° C; yield: 45–50%;

from 5-chloro-2-amino-pyridine and 2-formyl-phenyl-acetic acid ethyl ester α-phenyl-β-(5-chloro-2-pyridyl-amino)-acrylic acid ethyl ester, m.p.: 110°–112° C; yield: 50–55% are obtained.

EXAMPLE 5

10.8 g. (0.1 mole) of 3-methyl-2-amino-pyridine and 19.2 g. (0.1 mole) of 2-formyl-phenyl-acetic acid ethyl ester are heated to boiling in 100 ml. of n-butanol for 3 hours. After removing the solvent, the crude α-phenyl-β-(3-methyl-2-pyridyl-amino)-acrylic acid ethyl ester is crystallized from isopropanol. Yield: 30%, m.p.: 95°–97° C.

Analysis: C% 72.46 (calc. 72.32); H% 6.33 (calc. 6.43); N% 9.93 (calc. 9.92).

EXAMPLE 6

A mixture of 13.9 g. (0.1 mole) of 5-nitro-2-amino-pyridine and 19.2 g. (0.1 mole) of 2-formyl-phenylacetic acid ethyl ester is heated to boiling. The crude α-phenyl-β-(5-nitro-2-pyridyl-amino)-acrylic acid ethyl ester is crystallized from isopropanol. Yield: 60%; m.p.: 137°–140° C.

Analysis: C% 61.42 (calc. 61.35); H% 4.87 (calc. 4.82) N% 13.50 (calc. 13.41).

The above reaction is carried out by using 2-amino-quinoxaline as amine component. Thus α-phenyl-β-(2-quinoxalyl-amino)-acrylic acid ethyl ester is obtained. M.p.: 193°–194° C; yield: 60%.

EXAMPLE 7

The mixture of 14.4 g. (0.1 mole) of 2-amino-quinoline and 19.2 g. (0.1 mole) of 2-formyl-phenyl-acetic acid ethyl ester is heated to boiling in 150 ml. of toluene for 3 hours. After removing the solvent, the crude α-phenyl-β-(2-quinolyl-amino)-acrylic acid ethyl ester is recrystallized from toluene. Yield: 50–55%; m.p.: 181°–182° C.

Analysis: C% 75.31 (calc. 75.51); H% 5.48 (calc. 5.69); N% 9.09 (calc. 8.81).

The above condensation is carried out by using 2-formyl-propionic acid ethyl ester as formyl-acetic acid component. Thus α-methyl-β-(2-quinolyl-amino)-acrylic acid ethyl ester is obtained. M.p.: 164°–165° C; yield: 60%.

What we claim is:

1. A compound of the formula

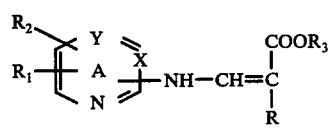

and tautomeric forms thereof or a hydrochloric acid, sulfuric acid, phosphoric acid, perchloric acid, citric acid, amygdalic acid or malic acid salt thereof, R being selected from the group which consists of methyl, ethyl, phenyl, benzyl, $CH_2COOC_2H_5$, $-(CH_2)_2COOC_2H_5$, and $-(CH_2)_3COOC_2H_5$:

$R_1$ and $R_2$ each being hydrogen or together forming a $-CH=CH-CH=CH-$ group attached at the 2 and 3 or the 3 and 4 positions to the ring A;

X and Y being $-CH=$ or $-N=$ with at least one of X and Y being $-CH=$;

$R_3$ being H or $CH_3$; and ring A being unsubstituted or substituted with a substituent selected from the group consisting of methyl, ethyl, propyl, nitro chloro, bromo, hydroxyl, methoxy, ethoxy, carboxy ethoxycarbonyl, carboxamido, amino, methylamino, dimethylamino and acetylamino.

2. The compound α-(ethoxycarbonyl-methyl)-β-2-pyridyl-amino)-acrylic acid ethyl ester.

* * * * *